United States Patent [19]

Horwell et al.

[11] Patent Number: 4,579,863

[45] Date of Patent: Apr. 1, 1986

[54] SUBSTITUTED TRANS-1,2-DIAMINOCYCLOHEXYL AMIDE COMPOUNDS

[75] Inventors: David C. Horwell, Foxton; Andrew Beeby, Norwich, both of England

[73] Assignee: Warner-Lambert Company, Morris Plains, N.J.

[21] Appl. No.: 558,736

[22] Filed: Dec. 6, 1983

[51] Int. Cl.⁴ .................. C07D 401/08; C07D 403/08; C07D 407/08; C07C 103/24; A61K 31/165; A61K 31/34; A61K 31/40; A61K 31/445

[52] U.S. Cl. ................................... 514/422; 514/316; 514/471; 514/616; 548/523; 546/190; 564/156; 549/473

[58] Field of Search .................. 548/523; 546/190; 564/156; 514/316, 422, 471, 616; 549/473

[56] References Cited

U.S. PATENT DOCUMENTS

| | | | |
|---|---|---|---|
| 4,098,904 | 7/1978 | Szmuszkovicz | 548/578 X |
| 4,145,435 | 3/1979 | Szmuszkovicz | 548/578 X |
| 4,390,679 | 6/1983 | Weiss et al. | 528/64 |

*Primary Examiner*—Mark L. Berch
*Assistant Examiner*—William A. Teoli, Jr
*Attorney, Agent, or Firm*—Jerry F. Janssen

[57] ABSTRACT

Substituted trans-1,2-diaminocyclohexyl amide compounds demonstrating selective opioid receptor binding possess utility as analgesic, diuretic, and psychotherapeutic agents. A method of preparing the compounds, pharmaceutical compositions employing the compounds, and a method of alleviating pain employing the compounds are also disclosed.

9 Claims, No Drawings

SUBSTITUTED TRANS-1,2-DIAMINOCYCLOHEXYL AMIDE COMPOUNDS

BACKGROUND OF THE INVENTION

The search for strong analgesics which also possess minimal potential for dependency has been among the highest priority efforts in pharmacological research. These research efforts have, to a great extent, involved chemical modifications of the opiate structure and the discovery of chemically novel compounds which possess morphine-like activity.

The discovery of endogenous opioids has led workers in the field to consider that these peptides, possessing less rigid structures, might interact with opioid receptors other than those to which the classical rigid structure opiates, such as morphine, bind.

The concept of multiple opioid receptors has been supported by studies with nalorphine and a series of benzomorphans which display unusual pharmacological properties dissimilar from morphine, yet blocked by the selective opioid antagonists. [See, for example, W. R. Martin, et al., *J. Pharmacol. Exp. Ther.*, 197: 517–532 (1976)].

The existence of multiple types of opioid receptors is of importance because it suggests the possibility of separating the desirable analgesic and psychotherapeutic effects of a drug compound from the undesirable abuse potential or habituating effects.

U.S. Pat. No. 4,145,435 describes certain 2-aminocycloaliphatic amide compounds as analgesics. In particular, trans-3,4-dichloro-N-methyl-N-[2-(1-pyrrolidinyl)-cyclohexyl]-benzacetamide has been reported to possess selective kappa agonist activity, and therefore to possess analgesic activity without attendant dependence liability. [See P. V. Vanvoigtlander, et al., *J. Pharmacol. Exp. Ther.*, 224: 7–12 (1983)].

Recently, the diuretic effect of various opioid agonists and antagonists has been studied, and it has been shown that kappa agonists tend to increase urination, while mu agonists decreased urination. [See J. D. Leander, *J. Pharmacol. Exp. Ther.*, 227: 35–41 (1983)]. These findings suggest that selective opioid agonists and antagonists also possess potential as diuretics.

SUMMARY OF THE INVENTION

The present invention relates to substituted trans-1,2-diamino-cyclohexylamide compounds useful as analgesics, diuretics, and psychotherapeutic agents. The invention is also concerned with a method of preparing such compounds, pharmaceutical compositions including such compounds, and with a method of alleviating pain in a mammal by administering an effective amount of a pharmaceutical composition in accordance with the present invention.

In its broadest aspect, the present invention encompasses compounds having structural formula I

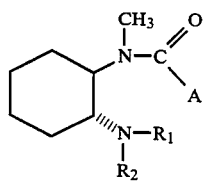

where $R_1$ is methyl and $R_2$ is hydrogen, alkyl of from one to six carbon atoms,

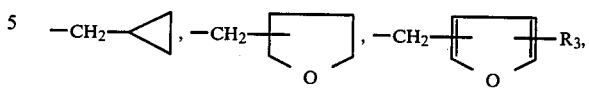

$-CH_2C \equiv CR_3R_4$ where $R_3$ and $R_4$ are independently hydrogen or methyl, or where $R_1$ and $R_2$ taken together with the nitrogen atom to which they are attached comprise a 5- or 6-membered ring; and wherein A is

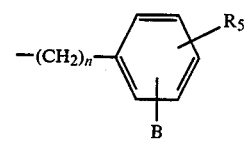

where n is an integer of from one to six; $R_5$ is hydrogen, fluorine, chlorine, nitro, alkyl of from one to six carbon atoms, or alkoxy of from one to six carbon atoms; and B is

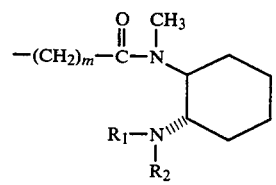

where m is an integer of from one to six; and the pharmaceutically acceptable acid addition salts thereof.

In accordance with a second aspect of the present invention, a method preparing compounds having structural formula I comprising reacting at least two molar equivalents of a substituted trans-cyclohexyldiamine of structure II

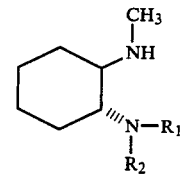

with one molar equivalent of a substituted dicarboxylic acid of structural formula III.

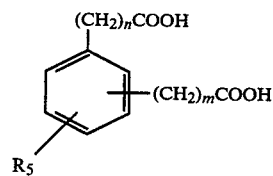

In accordance with another aspect of the present invention, pharmaceutical compositions useful for the alleviation of pain in a mammal comprise an effective amount of a compound having structural formula I above, in combination with a pharmaceutically acceptable carrier.

In a further aspect of the present invention, a method of alleviating pain in a mammal comprises administering to a mammal suffering from pain an effective amount of a pharmaceutical composition, preferably in unit dosage form, which composition includes a compound having structural formula I, above, in combination with a pharmaceutically acceptable carrier.

DETAILED DESCRIPTION

Compounds of the present invention comprise a class of derivatives of trans-1,2-diaminocyclohexane in which one nitrogen is a tertiary amine nitrogen substituted with methyl and a substituent selected from the group $R_2$ as defined above or, preferably is a tertiary amine nitrogen attached to the cyclohexane ring and which is part of a pyrrolidinyl or piperidinyl group. The other nitrogen atom of the 1,2-diaminocyclohexane is an N-methyl amide nitrogen.

In the structural formula for subunit "A" given above, the bonds attaching the polymethylene group and "B" to the aromatic ring may be attached to the ring in positions which are ortho, meta, or para with respect to one another, but preferably ortho.

By the term "alkyl of from one to six carbon atoms" as used throughout this specification and the appended claims is meant branched or unbranched saturated hydrocarbon groupings containing one to six carbon atoms. Examples include methyl, ethyl, n-propyl, iso-propyl, n-butyl, sec-butyl, iso-butyl, n-pentyl, and the like.

By the term "alkoxy" is meant a branched or unbranched hydrocarbon grouping such as "alkyl" as defined above, attached to an oxygen atom.

Compounds of the present invention may contain one or more asymmetric carbon atoms and thus exist as enantiomers or diastereomers. The present invention contemplates all possible optical isomeric forms of structural formula I given above. Individual enantiomorphic or diastereomeric forms of the compounds of this invention may be obtained from mixtures by known methods of resolution.

In a preferred embodiment, compounds of formula I are those wherein m is equal to n.

In another preferred embodiment, compounds of formula I are those wherein $R_5$ is hydrogen.

One specific embodiment is a compound having the name trans, trans-N,N'-dimethyl-N,N'-bis[2-(1-pyrrolidinyl)cyclohexyl]-1,2-benzenediacetamide; and the pharmaceutically acceptable acid addition salts thereof.

In general, compounds of the present invention are prepared by reacting at least two molar equivalents of the appropriate trans-1,2-diaminocyclohexane of structural formula II with one molar equivalent of a dicarboxylic acid of structural formula III

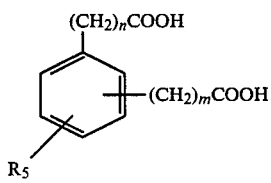

or a reactive derivative formed from such a dicarboxylic acid.

The appropriate dicarboxylic acid (III) may be reacted directly with the amine with the aid of such reagents as dicyclohexylcarbodiimide and the like. Alternatively, the dicarboxylic acids are first converted to a reactive derivative such as an activated ester, anhydride, acid halide such as the bromide or chloride, or acyl imidazoles of the formula IV

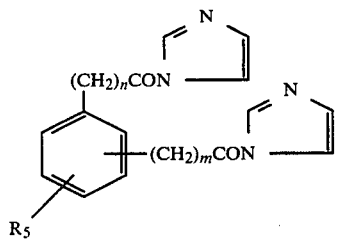

and the resulting dicarboxylic acid derivative reacted with the substituted trans-1,2-diaminocyclohexane (II).

For example the reaction between the cyclic diamine (II) and the appropriate dicarboxylic acid (III) is carried out in the presence of the coupling reagent, dicyclohexylcarbodiimide, in a cyclic ether solvent such as tetrahydrofuran or dioxane until the desired product is formed. The reaction will generally proceed at ambient temperatures but, depending upon the reactivity of the specific materials involved, the desired reaction time, the solvent being employed, and the molar proportions of reagents, the reaction temperature may be varied between about $-25°$ C. and the reflux temperature of the solvent employed.

The reaction between the diacid halide and the cyclic diamine (II) is carried out, generally at ambient temperature, in a suitable solvent in the presence of an acid acceptor such as a tertiary amine or an alkali metal or alkaline earth metal carbonate or bicarbonate. The mixture of the amine and the diacid halide is allowed to stand until reaction is complete.

When the reaction between the cyclic diamine (II) and the diacid (III) or diacid derivative has proceeded to substantial completion, the desired product is recovered from the reaction mixture by techniques well known to practitioners of the organic chemical arts.

For example, the reaction mixture can be evaporated under vacuum, if desired, to remove the solvent and other volatile components of the reaction mixture to yield the product, generally as an oil. This residual material is then taken up in a solvent such as diethyl ether, washed first with a salt solution such as sodium bicarbonate solution and then with water. Separation of the organic phase, drying over, for example anhydrous magnesium sulfate, and evaporation of the ether solvent, yields the desired product, usually as an oil or crystalline solid.

The starting trans-1,2-diaminocyclohexane compounds of the present invention are prepared by the method detailed in U.S. Pat. No. 4,145,435. The dicarboxylic acids (III) are known, or if novel, are prepared by reaction sequences well known in the art. The acyl imidazole derivatives (IV) of the dicarboxylic acids are prepared by reacting carbonyldiimidazole with the appropriate diacid.

The free base form of the compounds of this invention are readily converted, if desired, by known methods to the acid addition salts by reaction with any of a number of inorganic or organic acids including hydrochloric, hydrobromic, hydriodic, sulfuric, nitric, phosphoric, acetic, benzoic, citric, maleic, tartaric, succinic, gluconic, ascorbic, sulphamic, oxalic, pamoic, methanesulfonic, benzenesulfonic, and related acids and mixtures thereof. The free base form of the compounds of the present invention and the acid addition salt may differ in certain of their physical properties, such as solubility in polar solvents, but are otherwise equivalent for the purposes of this invention.

The compounds of the present invention possess significant analgesic activity with potential for minimum dependence liability due to their selective kappa opioid receptor binding properties. In addition to analgesics, selective kappa agonists also cause opioid receptor-mediated sedation, diuresis, and corticosteroid evaluations. Accordingly, the compounds of the present invention may also be useful diuretics and psychotherapeutic agents as well as analgesics.

A representative example of the compounds of formula I has shown positive activity in standard laboratory analgesic tests such as acetylcholine-induced writhing and hot plate with animals such as mice. Abolition of writhing was observed in mice at subcutaneous doses of 100 mg/kg of animal body weight of the compound of Example 1. When compared with control, mice showed longer tolerance, greater than 10 seconds (maximum determined at 40 seconds from control) on a hot plate at 55° C. when given 100 mg/kg of the compound of Example 1 subcutaneously.

A representative example of the compounds of the present invention, when tested in vitro to determine the extent of opioid receptor binding, was found to be selectively bound to the kappa receptors with evidence of little or no binding to the mu and delta receptors. The benefits of this selective binding has already been mentioned above and is also described by M. B. Tyers, *Br. J. Pharmac.* (1980) 69: 503–512.

The compounds of the present invention, and/or the nontoxic, pharmaceutically acceptable salts thereof, may be administered to mammals in pharmaceutical compositions or formulations which comprise one or more of the compounds of this invention and/or the nontoxic, pharmaceutically acceptable, nontoxic carrier.

The compounds of this invention may be administered parenterally in combination with conventional injectable liquid carriers such as sterile pyrogen-free water, sterile peroxide-free ethyl oleate, dehydrated alcohols, propylene glycol, and mixtures thereof.

Suitable pharmaceutical adjuvants for the injecting solutions include stabilizing agents, solubilizing agents, buffers, and viscosity regulators. Examples of these adjuvants include ethanol, ethylenediamine tetraacetic acid (EDTA), tartrate buffers, citrate buffers, and high molecular weight polyethylene oxide viscosity regulators. These pharmaceutical formulations may be injected intramuscularly, intraperitoneally, or intravenously, or intravenously.

Compounds of the present invention, and/or the nontoxic, pharmaceutically acceptable salts thereof, may be administered to mammals orally in combination with conventionally compatible carriers in solid or in liquid form. These oral pharmaceutical compositions may contain conventional ingredients such as binding agents selected form the group consisting of syrups, acacia, gelatin, sorbitol, tragacanth, polyvinylpyyrolidone, and mixtures thereof. The compositions may further include fillers such as lactose, mannitols, starch, calcium phosphate, sorbitol, methylcellulose, and mixtures thereof.

These oral compositions may also contain lubricants such as magnesium stearate, high molecular weight polymers such as polyethylene glycol, high molecular weight fatty acids such as stearic acid silica, or agents to facilitate disintegration of the solid formulation, such as starch, and wetting agents such as sodium lauryl sulfate.

The oral pharmaceutical compositions may take any convenient form such as tablets, capsule, lozenges, aqueous or oily suspensions, emulsions, or even dry powders which may be reconstituted with water and/or other liquid media prior to use.

Compounds of the present invention and/or the nontoxic, pharmaceutically acceptable salts thereof may be administered topically in the form of an ointment or cream containing from about 0.1% to 10% by weight of the active component in a pharmaceutical ointment or cream base.

Compounds of the present invention and/or the nontoxic, pharmaceutically acceptable salts thereof, may be administered to mammals rectally in the form of suppositories. For preparing suppositories, a low-melting wax such as a mixture of fatty acid glycerides or cocoa butter is first melted, and the active ingredient is dispersed homogeneously therein by stirring. The molten homogeneous mixture is then poured into convenient sized molds, allowed to cool and thereby solidify.

The solid or liquid forms may contain flavorants, sweeteners, and/or preservatives such as alkyl p-hydroxybenzoates. The liquid forms may further contain suspending agents such as sorbitol, glucose, or other sugar syrups, methyl-, hydroxymethyl-, or carboxymethylcellulose, and gelatin, emulsifying agents such as lecithin or sorbitol monooleate, and conventional thickening agents. The liquid compositions may optionally be encapsulated in, for example, gelatin capsules, in an effective amount.

Preferably, the pharmaceutical compositions of this invention are in unit dosage form. In such form, the preparation is subdivided into unit doses containing appropriate amounts of the active component. The unit doses form can be a packaged preparation with the package containing discrete quantities of the preparation. For example, the package may take the form of packeted tablets, capsules, and powders in envelopes, vials or ampoules. The unit dosage form can also be a capsule, cachet, or tablet itself or can be the appropriate number of any of these packaged forms.

The quantity of active compound in a unit dose of preparation may be varied or adjusted from 0.5 mg to about 350 mg according to the particular application and the potency of the active ingredient.

When employed systematically in therapeutic use as analgesic agents in the pharmaceutical method of this invention, the compounds are administered at doses of about 0.05 mg to 2.0 mg of active compound per kilogram of body weight of the recipient.

The following example is provided to enable one skilled in the art to practice the present invention. The examples are not to be read as limiting the scope of the invention as defined by the appended claims, but as merely illustrative thereof.

EXAMPLE 1

Preparation of trans, trans-N,N'-dimethyl-bis[2-(1-pyrrolidinyl)cyclohexyl]-1,2-benzenediacetamide A. Preparation of 7-methyl-7-azabicyclo[4.1.0]heptane [Modification of method of T. Taguchi and M. Eto, *J. Amer. Chem. Soc.* 80: 4076 (1958)]

i. Cyclohexene oxide (Aldrich, 196.3 g 2M) was added to a 25/30% solution of aqueous methylamine (745 ml, 6M) (25% solution) dropwise with stirring and cooling in an icebath over one hour, during which time the temperature reached 46° C. The solution was stirred at room temperature overnight, and then refluxed for three hours in fume hood. The solution was cooled in an icebath and saturated with solid NaOH, extracted with 4×200 ml ether, dried (MgSO4) and evaporated to dryness on rotary evaporator.

The crude product was distilled under water vacuum pressure, the first small sample of cyclohexene epoxide discarded. The bulk was distilled from a 1-liter flask with a 60 W isomantle and a short Leibig condenser over a two hour period to yield the product.

bp 118° C. (water vacuum)
yield: 208 g (81%)

ii. Trans-2-(methylamino)cyclohexanol (208 g, 1.61M) was placed in a three liter beaker and dissolved in ether (400 ml). Chlorosulphonic acid (1.89 g, 1.62M) was added dropwise to the ice-salt cooled solution. Added a further 200 ml of ether. The solution was hand stirred. Addition took one hour. The solution/solid was allowed to warm to room temperature and stand for three hours. The ether was decanted and the white salt washed with 300 ml ether which was also decanted.

The solid was cooled in ice-salt bath and NaOH (218 g in one liter water) added slowly. The thick white solid was left at room temperature overnight.

The crude product was distilled in Isomantle with continuous addition of water from separating funnel to retain approximately original volume. After 600 ml of liquid had been collected, the total distillate was saturated with solid NaOH, extracted with 5×200 ml ether, dried (MgSO4) and evaporated on rotary evaporator.

The product was distilled using a water vacuum and air bleed, the collection vessel being cooled in an ice bath.

yield: 67 g (37%), b.p. 38° C. (water vacuum and bleed)

iii. Preparation of trans N-methyl-2-(1-pyrrolidinyl)-cyclohexanamine

A mixture of 7-Methyl-7-azabicyclo[4.1.0]heptane (7.0 g, 0.063M), pyrrolidine (17.92 g, 0.25M), water (10 ml) and ammonium chloride (0.16 g) was stirred and refluxed for 21 hours. The solution was cooled and solid sodium hydroxide added and extracted with ether (3×50 ml). The extracts were dried over magnesium sulphate and evaporated under reduced pressure to a brown oil. This was distilled under high vacuum to yield a colorless oil.

b.p.: 95° C. (6.0 g)

B. Trans, trans-N,N'-dimethyl-N,N'-bis-[2-(1-pyrrolidinyl)cyclohexyl]-1,2-benzenediacetamide, dihydrochloride Trans-N-methyl-2-(1-pyrrolidinyl)-cyclohexanamine (0.365 g) was dissolved in methylene chloride (10 ml) and stirred at room temperature. The di-acid chloride of ortho-phenylenediacetic acid (prepared by the action of thionyl chloride on ortho-phenylenediacetic acid, 0.194 g) dissolved in methylene chloride (10 ml) was added and let stand for 0.5 hour. Ether was added to rapidly stirred solution until no more precipitate appeared. After further rapid stirring for one hour, the precipitate was filtered and dried in a vacuum oven at 90° C. for one hour and stored in a predried bottle. The product was in the form of a white solid (400 mg), mp 261°–263° C.

We claim:

1. A compound having the structural formula

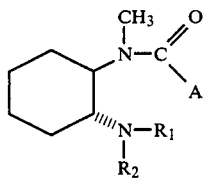

where $R_1$ is methyl and $R_2$ is hydrogen, alkyl of from one to six carbon atoms,

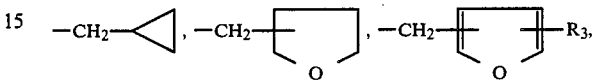

—$CH_2C\!\!=\!\!CR_3R_4$ where $R_3$ and $R_4$ are independently hydrogen or methyl, or where $R_1$ and $R_2$ taken together with the nitrogen atom to which they are attached from a pyrrolidinyl or piperadinyl ring; and wherein A is

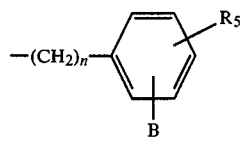

where n is an integer of from one to six; $R_5$ is hydrogen, fluorine, chlorine, nitro, alkyl of from one to six carbon atoms, or alkoxy of from one to six carbon atoms; and B is

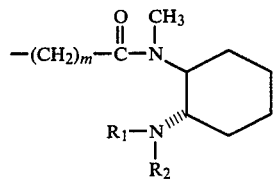

where m is an integer of from one to six; and the pharmaceutically acceptable acid addition salts thereof.

2. A compound in accordance with claim 1 having the formula

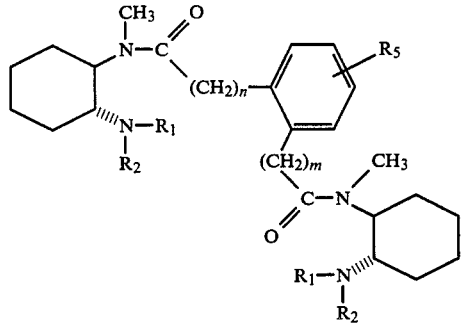

wherein m, n, $R_1$, $R_2$ and $R_5$ are as defined above, and the pharmaceutically acceptable acid addition salts thereof.

3. A compound in accordance with claim 2 wherein $R_1$ and $R_2$ taken together with the nitrogen atom to which they are attached form a pyrrolidinyl or piperidinyl ring; and the pharmaceutically acceptable acid addition salts thereof.

4. A compound in accordance with claim 3 wherein m is equal to n.

5. A compound in accordance with claim 4 wherein $R_5$ is hydrogen.

6. A compound having the name trans, trans-N,N'-dimethyl-N,N'-bis[2-(1-pyrrolidinyl)cyclohexyl]-1,2-benzenediacetamide; and the pharmaceutically acceptable acid addition salts thereof.

7. A compound having the name trans, trans-N,N'-dimethyl-N,N'-bis[2-(1-pyrrolidinyl)cyclohexyl]-1,2-benzenediacetamide dihydrochloride.

8. A pharmaceutical composition useful for alleviating pain in a mammal, said composition comprising an effective amount of a compound in accordance with claim 1 in combination with a pharmaceutically acceptable carrier.

9. A method of alleviating pain in a mammal in need of such treatment, said method comprising administering to said mammal a pharmaceutical composition in accordance with claim 8 in unit dosage form.

* * * * *